United States Patent [19]

Scherkenbeck et al.

[11] Patent Number: 5,216,180

[45] Date of Patent: Jun. 1, 1993

[54] MICROBICIDAL HYDROXYETHYL-CYCLOPROPYL-AZOLYL DERIVATIVES

[75] Inventors: Jürgen Scherkenbeck, Leverkusen; Monika Frie, Odenthal-Osenau; Klaus Stroech, Solingen; Thomas Himmler, Cologne; Georg-W. Ludwig, Krefeld; Wilhelm Brandes, Leichlingen; Stefan Dutzmann, Duesseldorf, all of Fed. Rep. of Germany

[73] Assignee: Bayer Aktiengesellschaft, Leverkusen, Fed. Rep. of Germany

[21] Appl. No.: 786,481

[22] Filed: Nov. 1, 1991

Related U.S. Application Data

[62] Division of Ser. No. 535,266, Jun. 8, 1990, Pat. No. 5,096,912.

[30] Foreign Application Priority Data

Jun. 30, 1989 [DE] Fed. Rep. of Germany ....... 3921481

[51] Int. Cl.$^5$ .................. C07D 317/06; C07D 303/16
[52] U.S. Cl. ..................................... 549/435; 549/60; 549/504; 549/497; 549/551; 549/534; 549/556; 549/555; 549/560; 549/563
[58] Field of Search ............... 549/551, 556, 555, 512, 549/560, 563, 60, 492, 554, 435, 504

[56] References Cited

U.S. PATENT DOCUMENTS

| | | | |
|---|---|---|---|
| 4,507,140 | 3/1985 | Sugavanam | 548/140 |
| 4,845,250 | 7/1989 | Sugavanam | 549/563 |
| 4,921,528 | 5/1990 | Bockmann et al. | 548/267.8 |
| 4,925,482 | 5/1990 | Stroech et al. | 548/267.8 |
| 4,925,865 | 3/1990 | Stroech et al. | 548/266.4 |
| 4,946,493 | 8/1990 | Sugavanam | 71/76 |
| 4,965,281 | 10/1990 | Cuomo et al. | 549/60 |
| 4,980,488 | 12/1990 | Stroech et al. | 549/554 |
| 4,983,208 | 1/1991 | Stroech et al. | 548/101 |
| 5,079,374 | 1/1992 | Stroech et al. | 549/563 |

FOREIGN PATENT DOCUMENTS 336186 10/1989 European Pat. Off.

OTHER PUBLICATIONS

Bagdar, et al., *Chemical Abstracts* 110: 130439a, pp. 265-266, (1989).
Thomas, et al., *Chemical Abstracts* 110: 53769d, p. 326 (1989).
Heindel et al., *Chemical Abstracts* 99: 158,113t p. 588 (1983).
Shoho et al., *Chemical Abstracts* 77: 15,650h, p. 324 (1972).

*Primary Examiner*—Allen J. Robinson
*Assistant Examiner*—M. W. Russell
*Attorney, Agent, or Firm*—Sprung, Horn Kramer & Woods

[57] ABSTRACT

A herbicidal hydroxyethyl-cyclopropyl-azolyl derivative of the formula in which
$R^1$ represents halogen, phenyl or the grouping $-Z-R^3$, wherein
Z represents oxygen, sulphur, SO or SO$_2$ and
$R^3$ represents alkyl, phenyl or benzyl,
$R^2$ represents alkenyl, optionally substituted furyl, optionally substituted thienyl or the radical of the formula wherein
$R^4$ represents difluoromethoxy, 1,1,2,2-tetrafluoroethoxy, 1,1,2-trifluoro-2-chloro-ethoxy, cyano, formyl, alkoximinoalkyl, carbalkoxy, dialkoxyalkyl, phenoxyalkyl which is optionally substituted in the phenyl moiety by halogen, or benzyloxy which is optionally substituted in the phenyl moiety by halogen and
$R^5$ represents hydrogen or halogen, or
$R^4$ and $R^5$ are linked in the ortho-position and together represent $-O-CH_2-O-$, or
$R^2$ represents the radical of the formula in which
$R^6$ represents difluoromethoxy, 1,1,2,2-tetrafluoroethoxy or 1,1,2-trifluoro-2-chloro-ethoxy, or
$R^2$ also represents phenyl which is optionally substituted by halogen and/or phenyl if Y represents the grouping $-CH-CH-$ with O bridge, X represents nitrogen or a CH group and
Y represents the groupings $-CH_2-CH_2-$, $-CH=CH-$, $-C\equiv C-$ or $-CH-CH-$ with O bridge, or an acid or metal salt addition product thereof.

6 Claims, No Drawings

MICROBICIDAL HYDROXYETHYL-CYCLOPROPYL-AZOLYL DERIVATIVES

This is a division of application Ser. No. 535,266, filed Jun. 8, 1990, now U.S. Pat. No. 5,096,912.

The present invention relates to new hydroxyethyl-cyclopropyl-azolyl derivatives, to a number of processes for their preparation and to their use as microbicides in plant protection and in the protection of materials.

It is already known that numerous hydroxyalkylazolyl derivatives have fungicidal properties (cf. EP-OS (European Published Specification) 0,298,332). Thus, for example, 1-(4-trifluoromethoxyphenyl)-3-(1-chloro-cycloprop-1-yl)-4-(1,2,4-triazol-1-yl)-but-1-en-3-ol and 1-(4-chlorophenyl)-3-(1-chloro-cycloprop-1-yl)-4-(1,2,4-triazol-1-yl)-butan-3-ol can be used for combating phytopathogenic fungi. The activity of these substances is good; however at low application rates the activity in some cases leaves something to be desired.

New hydroxyethyl-cyclopropyl-azolyl derivatives of the formula

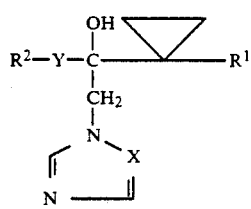

in which

R$^1$ represents halogen, phenyl or the grouping —Z—R$^3$, wherein

Z represents oxygen, sulphur, SO or SO$_2$ and

R$^3$ represents alkyl, phenyl or benzyl,

R$^2$ represents alkenyl, optionally substituted furyl, optionally substituted thienyl or the radical of the formula

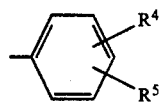

wherein

R$^4$ represents difluoromethoxy, 1,1,2,2-tetrafluoroethoxy, 1,1,2-trifluoro-2-chloro-ethoxy, cyano, formyl, alkoximinoalkyl, carbalkoxy, dialkoxyalkyl, phenoxyalkyl which is optionally substituted in the phenyl moiety by halogen, or benzyloxy which is optionally substituted in the phenyl moiety by halogen and R$^5$ represents hydrogen or halogen, or R$^4$ and R$^5$ are linked in the ortho-position and together represent —O—CH$_2$—O—, or R$^2$ represents the radical of the formula

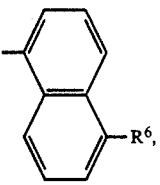

in which

R$^6$ represents difluoromethoxy, 1,1,2,2-tetrafluoroethoxy or 1,1,2-trifluoro-2-chloro-ethoxy, or R$^2$ also represents phenyl which is optionally substituted by halogen and/or phenyl if Y represents the grouping

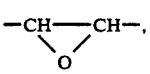

X represents nitrogen or a CH group and

Y represents the groupings —CH$_2$—CH$_2$—, —CH═CH—, —C≡C— or

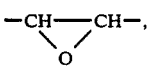

and their acid addition salts and metal salt complexes have now been found.

The substances according to the invention contain an asymmetrically substituted carbon atom. They can therefore be obtained in optical isomer forms. Moreover, those substances of the formula (I) in which Y represents a —CH═CH— group or a

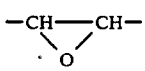

group can also be present in the form of cis or trans isomers. The invention relates both to the individual isomers and to their mixtures.

It has furthermore been found that hydroxyethyl-cyclopropyl-azolyl derivatives of the formula (I) and their acid addition salts and metal salt complexes are obtained when a) oxiranes of the formula

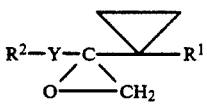

in which R$^1$, R$^2$ and Y have the abovementioned meanings, are reacted with azoles of the formula

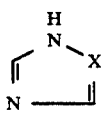

in which X has the abovementioned meaning, in the presence of an acid-binding agent and in the presence of a diluent, or b) ethanol derivatives of the formula

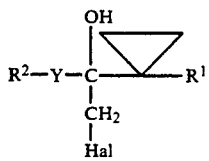
(IV)

in which
R¹, R² and Y have the abovementioned meanings, and
Hal represents chlorine, bromine or iodine,
are reacted with azoles of the formula

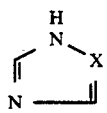
(III)

in which X has the abovementioned meaning, in the presence of an acid-binding agent and in the presence of a diluent, or c) hydroxyethyl-cyclopropyl-azolyl derivatives of the formula

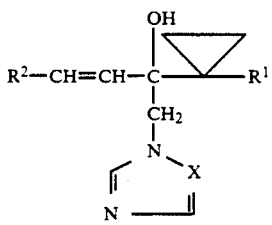
(Ia)

in which R¹, R² and X have the abovementioned meanings, are reacted with a reagent suitable for epoxidation, if appropriate in the presence of a diluent, and, if appropriate, an acid or a metal salt is then adducted to the compounds of the formula (I) thus obtained.

Finally, it has been found that the new hydroxyethyl-cyclopropyl-azolyl derivatives of the formula (I) and their acid addition salts and metal salt complexes have very good microbicidal properties and can be used both in plant protection and also in the protection of materials.

Surprisingly, the substances according to the invention show a distinctly better activity in combating phytopathogenic fungi than 1-(4-trifluoromethoxyphenyl)-3-(1-chloro-cycloprop-1-yl)-4-(1,2,4-triazol-1-yl)-but-1-en-ol and 1-(4-chloro-phenyl)-3-(1-chloro-cycloprop-1-yl)-4-(1,2,4-triazol-1-yl)-butan-3-ol, which are previously known compounds of similar constitution and with the same type of action.

Formula (I) provides a general definition of the hydroxyethyl-cyclopropyl-azolyl derivatives according to the invention. Preferably, in this formula
R¹ represents fluorine, chlorine, bromine, phenyl or the grouping —Z—R³, wherein
Z represents oxygen, sulphur, SO or SO₂ and
R³ represents alkyl having 1 to 6 carbon atoms, phenyl or benzyl,
R² represents straight-chain or branched alkenyl having 2 to 8 carbon atoms, furyl which is optionally substituted by halogen or furyl, thienyl which is optionally substituted by halogen or the radical of the formula

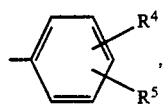

wherein
R⁴ represents difluoromethoxy, 1,1,2,2-tetrafluoroethoxy, 1,1,2-trifluoro-2-chloro-ethoxy, cyano, formyl, alkoximinoalkyl having 1 to 4 carbon atoms in the alkoxy group and 1 to 4 carbon atoms in the alkyl group, carbalkoxy having 1 to 4 carbon atoms in the alkoxy group, dialkoxyalkyl having 1 to 4 carbon atoms in each alkoxy group and 1 to 4 carbon atoms in the alkyl group, phenoxyalkyl having 1 to 4 carbon atoms in the alkyl group and which is optionally substituted in the phenyl moiety by fluorine and/or chlorine; or benzyloxy which is optionally substituted in the phenyl moiety by fluorine and/or chlorine and
R⁵ represents hydrogen, fluorine, chlorine or bromine, or
R⁴ and R⁵ are linked in the ortho-position and together represent —O—CH₂—O—, or
R² represents the radical of the formula

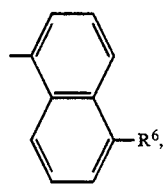

wherein
R⁶ represents difluoromethoxy, 1,1,2,2-tetrafluoroethoxy or 1,1,2-trifluoro-2-chloro-ethoxy, or
R² represents phenyl which is optionally substituted by fluorine, chlorine and/or phenyl if Y represents the grouping

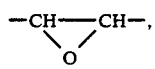

X represents hydrogen or a CH group and
Y represents the groupings —CH₂—CH₂—, —CH=CH—, —C≡C— or

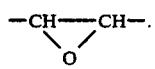

Particularly preferred compounds of the formula (I) are those in which
R¹ represents fluorine, chlorine, bromine, phenyl or the grouping —Z—R³, wherein
Z represents oxygen, sulphur, SO or SO₂ and
R³ represents alkyl having to 4 carbon atoms, phenyl or benzyl,
R² represents straight-chain or branched alkenyl having 3 to 6 carbon atoms, furyl which is optionally substituted by fluorine, chlorine, bromine or furyl, thienyl which is optionally substituted by fluorine, chlorine or bromine, or the radical of the formula

wherein

R⁴ represents difluoromethoxy, 1,1,2,2-tetrafluoroethoxy, 1,1,2-trifluoro-2-chloro-ethoxy, cyano, formyl, alkoximinoalkyl having 1 or 2 carbon atoms in the alkoxy group and 1 or 2 carbon atoms in the alkyl group, carbalkoxy having 1 or 2 carbon atoms in the alkoxy group, dialkoxyalkyl having 1 or 2 carbon atoms in each alkoxy group and 1 or 2 carbon atoms in the alkyl group, phenoxyalkyl having 1 or 2 carbon atoms in the alkyl group and optionally substituted in the phenyl moiety by fluorine and/or chlorine or benzyloxy which is optionally substituted in the phenyl moiety by fluorine and/or chlorine and R⁵ represents hydrogen, fluorine, chlorine or bromine, or R⁴ and R⁵ are linked in the ortho-position and together represent —O—CH₂—O—, or R² represents the radical of the formula

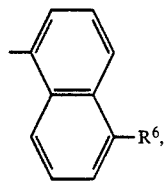

wherein

R⁶ represents difluoromethoxy, 1,1,2,2-tetrafluoroethoxy or 1,1,2-trifluoro-2-chloro-ethoxy, or R² also represents phenyl which is optionally substituted by fluorine, chlorine and/or phenyl if Y represents the grouping

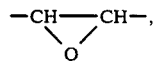

X represents nitrogen or a CH group and
Y represents the grouping —CH₂—CH₂—, —CH=CH—, —C≡C— or

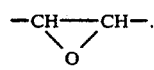

Preferred compounds according to the invention are also addition products of acids and those hydroxyethyl-cyclopropyl-azolyl derivatives of the formula (I) in which R¹, R², X and Y have the meanings which have already been mentioned as being preferred for these radicals.

The acids which can be adducted preferably include hydrohalic acids such as, for example, hydrochloric acid and hydrobromic acid, in particular hydrochloric acid, and further phosphoric acid, nitric acid, sulphuric acid, mono- and bifunctional carboxylic acids and hydroxycarboxylic acids, such as, for example, acetic acid, maleic acid, succinic acid, furaric acid, tartaric acid, citric acid, salicyclic acid, sorbic acid and lactic acid and also sulphoic acids, such as, for example, p-toluene-sulphonic acid, 1,5-naphthalenedisulphonic acid or camphorsulphonic acid.

Additionally preferred compounds according to the invention are addition products of salts of metals of main groups II to IV and subgroups I and II and also IV to VIII of the Periodic Table of the elements and those hydroxyethyl-cyclopropyl-azolyl derivatives of the formula (I) in which R¹, R², X and Y have the meanings which have already been mentioned as being preferred for these radicals.

In this connection, salts of copper, zinc, manganese, magnesium, tin, iron and nickel are particularly preferred. Suitable anions of these salts are those which are derived from those acids which lead to physiologically tolerated addition products.

Particularly preferred acids of this type in this connection are the hydrohalic acids, such as, for example, hydrochloric acid and hydrobromic acid, and further phosphoric acid, nitric acid and sulphuric acid.

If 2-(1-chloro-cycloprop-1-yl)-2-[4-(2-chloro-1,1,2-trifluoro-ethoxy)-phenyl-ethenyl]-oxiran and 1,2,4-triazole are used as starting materials, the course of process (a) according to the invention can be illustrated by the following equation:

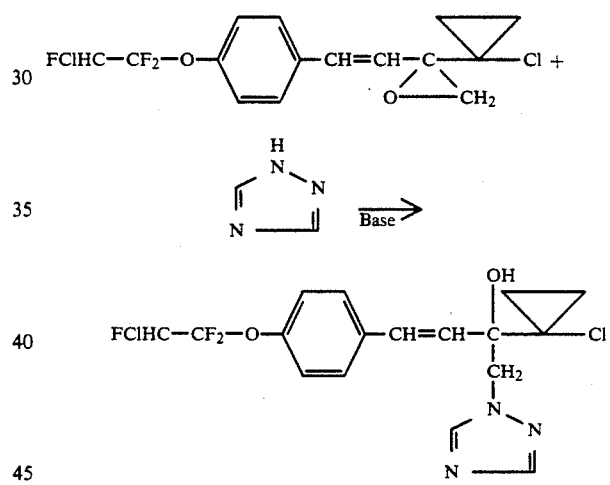

If 1-chloro-2-(1-chloro-cycloprop-1-yl)-4-(thiophen-2-yl)-but-3-in-2-ol and 1,2,4-triazole are used as starting materials, the course of process (b) according to the invention can be illustrated by the following equation:

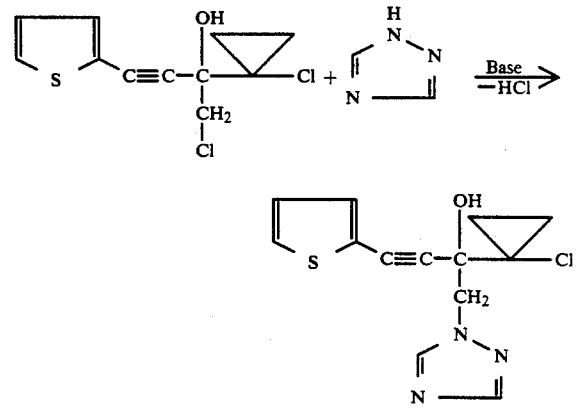

If 4-biphenylyl-2-(1-chloro-cycloprop-1-yl)-1-(1,2,4-triazol-1-yl)-but-3-en-2-ol is used as a starting material and 3-chloro-perbenzoic acid as an epoxidation reagent, the course of process (c) according to the invention can be illustrated by the following equation:

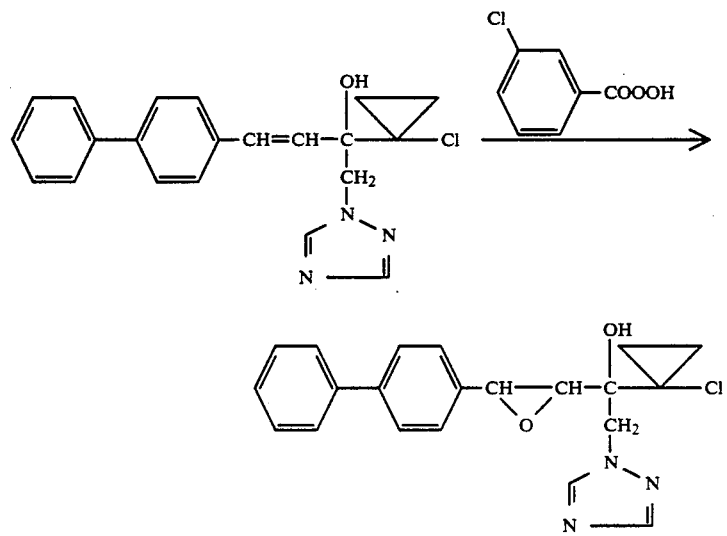

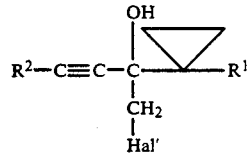  (IVa)

Formula (II) provides a general definition of the oxiranes required as starting materials for process (a) according to the invention. In this formula, $R^1$, $R^2$ and Y preferably have those meanings which have already been mentioned as being preferred for these radicals in connection with the description of the substances of the formula (I) according to the invention.

The oxiranes of the formula (II) were hitherto unknown. They can be prepared by a process in which
  d) cyclopropyl ketones of the formula

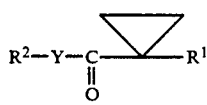  (V)

in which
  $R^1$, $R^2$ and Y have the abovementioned meanings, are reacted either
  α) with dimethyloxosulphonium methylide of the formula (CH₃)₂SOCH₂  $^{\delta\oplus\delta\ominus}$  (VI)

or
  β) with dimethylsulphonium methylide of the formula (CH₃)₂S CH₂  $^{\delta\oplus\delta\ominus}$  (VII)

in the presence of a diluent, or by a process in which
e) carbinols of the formula in which
  $R^1$ and $R^2$ have the abovementioned meanings and
  Hal' represents chlorine or bromine,
are reacted with bases in the presence of a diluent.

The cyclopropyl ketones of the formula (V) required as starting materials for carrying out process (d) were hitherto unknown. They can be prepared by a process in which
  f) aldehydes of the formula $R^2$—CHO    (VIII)

in which
  $R^2$ has the abovementioned meaning, are reacted with methyl cyclopropyl ketones of the formula

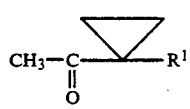  (IX)

in which
  $R^1$ has the abovementioned meaning, in the presence of a catalyst and in the presence of a diluent and, if appropriate, the resulting cyclopropyl ketones of the formula

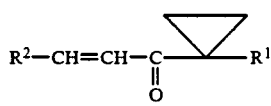  (V-a)

in which $R^1$ and $R^2$ have the abovementioned meanings, are either
  α) hydrogenated in the presence of a catalyst and in the presence of a diluent, or β) reacted with a reagent suitable for epoxidation, if appropriate in the presence of a diluent, or by a process in which g) acetylenes of the formula

  (X)

in which R² has the abovementioned meaning, are reacted with acid halides of the formula

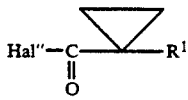  (XI)

in which

R¹ has the abovementioned meaning and

Hal" represents chlorine or bromine, in the presence of a catalyst and in the presence of a diluent.

The aldehydes of the formula (VIII) required as starting materials in process (f) are generally known compounds of organic chemistry.

The methyl cyclopropyl ketones of the formula (IX) additionally required as reaction components when carrying out process (f) are known or can be prepared by methods which are known in principle (cf. Synthesis 1977, 189).

Suitable catalysts for carrying out the first step of process (f) are all reaction accelerators which are customary for condensations of this type. Basic substances, for example alkali metal hydroxides, such as sodium hydroxide or potassium hydroxide are preferably utilizable.

Suitable diluents for carrying out the first step of process (f) are all inert organic solvents which are customary for reactions of this type. Alcohols, such as methanol, ethanol, isopropanol, n-butanol and tert.-butanol are preferably utilizable.

The reaction temperatures can be varied within a relatively wide range when carrying out the first step of process (f). In general, the reaction is carried out at temperatures between 0° C. and 100° C., preferably between 10° C. and 80° C.

The first step of process (f) is in general carried out under normal pressure. However, it is also possible to work at elevated or reduced pressure.

When carrying out the first step of process (f), 1 mole of aldehyde of the formula (VIII) and a catalytic amount of reaction accelerator are employed per mole of methyl cyclopropyl ketone of the formula (IX). However it is also possible to use one or the other component in an excess. Working up is carried out by customary methods. In general, a procedure is used in which the reaction products obtained in a solid state are filtered off with suction and are used for the further reactions, if necessary after prior purification.

In the second step of process (f), when working according to variant α, the cyclopropyl ketones of the formula (V-a) are hydrogenated with hydrogen in the presence of a catalyst and a diluent. In this case, the reaction is carried out in the liquid phase using a suspended pulverulent hydrogenation catalyst (heterogeneous) or using a catalyst complex soluble in the diluent (homogeneous). The hydrogenation can be carried out discontinuously (batchwise) or continuously as liquid-phase or trickle-phase hydrogenation in known hydrogenation reactors, such as autoclaves, autoclave cascades, tube reactors or recycling reactors. The preferred procedure is discontinuous liquid-phase hydrogenation in autoclaves at elevated pressure.

Suitable diluents for carrying out the second step of process (f, variant α) are inert organic solvents. These preferably include alcohols, such as methanol, ethanol, isopropanol or ethylene glycol; ethers, such as diethyl ether, diisopropyl ether, ethylene glycol monomethyl ether, ethylene glycol dimethyl ether, dioxane or tetrahydrofuran; saturated hydrocarbons, such as n-heptane or cyclohexane; aromatic hydrocarbons, such as toluene; and esters, such as ethyl acetate.

The reaction temperatures can be varied within a relatively wide range when carrying out the second step of process (f, variant α). In general the reaction is carried out at temperatures between 0° C. and 150° C., preferably between 20° C. and 120° C.

The hydrogenations in the second step of process (f, variant α) are carried out at normal pressure or also at elevated pressure. In general, the reaction is carried out under pressures between 1 and 150 bar, preferably between 5 and 60 bar.

Working up takes place by customary methods when carrying out the second step of process (f, variant α).

Suitable epoxidation agents for carrying out the second step of process (f, variant β) are all epoxidation reagents suitable for reactions of this type. Peracids, such as perbenzoic acid, 3-chloro-perbenzoic acid and peracetic acid, and additionally also hydrogen peroxide, are preferably utilizable.

Suitable diluents for carrying out the second step of process (f, variant β) are all solvents customary for reactions of this type. If the reaction is carried out with peracids, inert organic solvents, such as dichloromethane, are preferred. If hydrogen peroxide is used as the epoxidation agent, water or mixtures of water and inert organic solvents, such as dichloromethane, are preferably used.

The reaction temperatures can be varied within a certain range when carrying out the second step of process (f, variant β). In general, the reaction is carried out at temperatures between 0° C. and 40° C., preferably between 10° C. and 30° C.

When carrying out the second step of process (f, variant β), a procedure is in general used in which an equivalent amount or, also, an excess of epoxidation agent is employed per mole of cyclopropyl ketone of the formula (V-a). Working up is carried out by customary methods.

The acetylenes of the formula (X) required as starting substances for carrying out process (g) are known or can be prepared in a simple manner by methods which are known in principle.

The acid halides of the formula (XI) required as reaction components for carrying out process (g) are also known or can be prepared by methods which are known in principle.

Suitable catalysts for carrying out process (g) are all reaction accelerators which are customary for reactions of this type. Copper salts, such as, for example copper iodide, are preferably utilizable.

Suitable diluents for carrying out process (g) are all inert organic solvents which are customary for reactions of this type. Ethers such as tetrahydrofuran and diethylether, are preferably utilizable.

The reaction temperatures can be varied within a certain range when carrying out process (g) according to the invention. In general, the reaction is carried out at temperatures between −78° C. and +50° C., preferably between −78° C. and +40° C.

When carrying out process (g), in general 1 to 1.2 moles of acid halide of the formula (XI) and catalyst are employed per mole of acetylene of the formula (X). Working up is carried out by customary methods.

The dimethyl-oxo-sulphonium methylide of the formula (VI) required as a reaction component in process (d) is known (cf. J. Am. Chem. Soc. 87, 1363–1364 (1965)). It is processed in the above reaction in the freshly prepared state by generating it in situ by reaction of trimethyloxosulphonium iodide with sodium hydride or sodium amide, in particular with potassium tert.-butoxide or sodium methoxide, in the presence of a diluent.

The dimethylsulphonium methylide of the formula (VII) additionally possible as a reaction component is also known (cf. Heterocycles 8, 397 (1977)). It is also employed in the above reaction in the freshly prepared state by generating it in situ, for example from trimethylsulphonium halide or trimethylsulphonium methylsulphate, in the presence of a strong base, such as, for example, sodium hydride, sodium amide, sodium methoxide, potassium tert.-butoxide or potassium hydroxide, in the presence of a diluent, such as tert.-butanol or dimethyl sulphoxide.

Suitable diluents for carrying out process (d) are inert organic solvents. Alcohols, such as tert.-butanol, ethers, such as tetrahydrofuran or dioxane, and further aliphatic and aromatic hydrocarbons, such as benzene, toluene or xylene, and also strongly polar solvents, such as dimethyl sulphoxide, are preferably utilizable.

The reaction temperatures can be varied within a relatively wide range when carrying out process (d). In general, the reaction is carried out between 0° C. and 100° C., preferably between 10° C. and 60° C.

When carrying out process (d), in general 1 to 3 moles of dimethyloxosulphonium methylide of the formula (VI) or of dimethylsulphonium methylide of the formula (VII) are employed per mole of cyclopropyl ketone of the formula (V). The isolation of the oxiranes of the formula (II) is carried out by customary methods.

The carbinols of the formula (IV-a) required as starting materials for carrying out process (e) were hitherto unknown. They can be prepared by a process in which h) halogenoketones of the formula

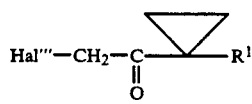

(XII)

in which

R$^1$ has the abovementioned meaning and

Hal''' represents chlorine or bromine, are reacted acetylene salts of the formula

(XIII)

in which

R$^2$ has the abovementioned meaning and

Me represents an equivalent of a metal cation, if appropriate in the presence of an acid-binding agent and in the presence of a diluent.

The halogenoketones of the formula (XII) required as starting substances in process (h) are known (cf. EP-OS (European Published Specification) 0,298,332).

Formula (XIII) provides a general definition of the acetylene salts required as reaction components in process (h). In this formula, R$^2$ preferably has those meanings which have already been mentioned as being preferred for this radical in connection with the description of the substances of the formula (I) according to the invention. Me preferably represents a lithium cation or an equivalent of a Cer(III) cation.

The acetylene salts of the formula (XIII) are known or can be prepared by methods which are known in principle.

Suitable acid-binding agents for carrying out process (h) are all customary acid acceptors.

Possible diluents for carrying out process (h) are all customary inert organic solvents. Aromatic hydrocarbons, such as toluene, and additionally ethers, such as diethyl ether, tetrahydrofuran, tert.-butyl methyl ether and mixtures of these ethers are preferably utilizable.

The reaction temperatures can be varied within a relatively wide range when carrying out process (h). In general, the reaction is carried out at temperatures between −100° C. and +100° C., preferably between −80° C. and +50° C.

Process (h) is in general carried out under normal pressure. However, it is also possible to work at elevated or reduced pressure.

When carrying out process (h), in general 1 to 3 moles of acetylene salt of the formula (XIII) are employed per mole of halogenoketone of the formula (XII). Working up is carried out by customary methods.

Possible bases for carrying out process (e) are all organic and inorganic acid-binding agents customarily suitable for reactions of this type. Alkali metal carbonates, such as sodium carbonate and potassium carbonate, further alkali metal hydroxides, such as sodium hydroxide and potassium hydroxide, additionally alkali metal alkoxides, such as sodium methoxide and potassium methoxide and sodium ethoxide and potassium ethoxide and also potassium tert.-butoxide, and furthermore lower tertiary alkylamines, cycloalkylamines and aralkylamines, such as, in particular, triethylamine, are preferably utilizable.

Possible diluents for carrying out process (e) are all customary inert organic solvents. Nitriles such as acetonitrile, further aromatic hydrocarbons, such as benzene, toluene and dichlorobenzene, additionally formamides, such as dimethylformamide, and also strongly polar solvents, such as dimethyl sulphoxide and hexamethylphosphoramide are preferably utilizable.

The reaction temperatures can be varied within a certain range when carrying out process (e). In general, the reaction is carried out at temperatures between −20° C. and +100° C., preferably between 0° C. and 60° C.

When carrying out process (e), the reaction is in general carried out under normal pressure. However, it is also possible to work at elevated or reduced pressure.

When carrying out process (e) in general 1 to 3 moles of base are employed per mole of carbinol of the formula (VI-a). Working up is carried out by customary methods.

The azoles of the formula (III) required as reaction components in process (a) according to the invention are generally known compounds of organic chemistry.

Suitable acid-binding agents for carrying out process (a) according to the invention are all customary acid acceptors. Alkali metal carbonates and hydrogen carbonates, such as sodium carbonates, potassium carbonate or sodium hydrogen carbonate, further alkali metal hydroxides and alkoxides, such as sodium hydroxide, potassium hydroxide, sodium methoxide or potassium tert.-butoxide, additionally tertiary aliphatic or aromatic amines, such as triethylamine, N,N-dimethyl-cyclohexylamine, N,N-dimethyl-benzylamine and pyridine, and additionally cyclic amines, such as 1,5-diaza-bicyclo[4.3.0]non-5-ene(DBN), 1,8-diaza-bicyclo[5.4.0]-undec-7-ene(DBU) and 1,4-diaza-bicyclo[2.2.2]octane (DABCO) are preferably utilizable.

Possible diluents for carrying out process (a) according to the invention are all customary inert organic solvents. Nitriles, such as, in particular, acetonitrile; aromatic hydrocarbons, such as benzene, toluene and dichlorobenzene; formamides, such as, in particular, dimethylformamide, and also hexamethylphosphoramide are preferably utilizable.

The reaction temperatures for carrying out process (a) according to the invention can be varied within a relatively wide range. In general, the reaction is carried out at temperatures between 0° C. and 200° C., preferably between 50° and 150° C.

When carrying out process (a) according to the invention, 1 to 4 moles of azole of the formula (III) and 1 to 2 moles of base are preferably employed per mole of oxirane of the formula (II). The isolation of the final products is carried out in a customary manner.

Formula (IV) provides a general definition of the ethanol derivatives required as starting substances for carrying out process (b) according to the invention. In this formula, $R^1$, $R^2$ and Y preferably have those meanings which have already been mentioned as being preferred for these radicals in connection with the description of the substances of the formula (I) according to the invention.

The ethanol derivatives of the formula (IV) were hitherto unknown. They can be prepared by process (h) if they are those substances in which Y represents —C≡C—. The other ethanol derivatives of the formula (IV) can be prepared from these substances of the formula (IV-a) by completely or partially hydrogenating the triple bond by customary methods or by epoxidizing those substances in which Y represents —CH=CH— by customary methods (cf. second step of process (f, variant β)).

When carrying out process (b) according to the invention, possible acid-binding agents are all customary acid acceptors. All those acid-binding agents which have already been mentioned in connection with the description of process (a) according to the invention are preferably utilizable.

Suitable diluents for carrying out process (b) according to the invention are all customary inert organic solvents. All those diluents which have already been mentioned in connection with the description of process (a) according to the invention are preferably utilizable.

The reaction temperatures can be varied within a relatively wide range when carrying out process (b) according to the invention. In general, the reaction is carried out at temperatures between 0° C. and 120° C., preferably between 20° C. and 100° C.

Process (b) according to the invention is in general carried out under normal pressure. However, it is also possible to work at elevated or reduced pressure.

When carrying out process (b) according to the invention, 1.5 to 3 moles of azole of the formula (III) and 3 to 6 moles of acid-binding agent are in general employed per mole of ethanol derivative of the formula (IV). Working up is carried out by customary methods.

When carrying out process (c) according to the invention, hydroxyethyl-cyclopropyl-azolyl derivatives of the formula (Ia) are employed as starting materials. These can be prepared by processes (a) or (b) according to the invention. The epoxidation by process (c) according to the invention is carried out in the same manner as the epoxidation in the second step of process (f, variant β).

The hydroxyethyl-cyclopropyl-azolyl derivatives of the formula (I) obtainable by the process according to the invention can be converted into acid addition salts or metal salt complexes.

In order to prepare acid addition salts of the compounds of the formula (I), those acids are preferred which have already been mentioned as preferred acids in connection with the description of the acid addition salts according to the invention.

The acid addition salts of the compounds of the formula (I) can be obtained in a simple manner by customary salt formation methods, for example by dissolving a compound of the formula (I) in a suitable inert solvent and adding the acid, for example hydrochloric acid, and are isolated in a known manner, for example by filtering off, and, if appropriate, are purified by washing with an inert organic solvent.

In order to prepare metal salt complexes of the compounds of the formula (I), those salts of metals are preferred which have already been mentioned as preferred metal salts in connection with the description of the metal salt complexes according to the invention The metal salt complexes of the compounds of the formula (I) can be prepared in a simple manner by customary methods, for example by dissolving the metal salt in alcohol, for example ethanol and adding to compounds of the formula (I). Metal salt complexes can be isolated in a known manner, for example by filtering off, and if appropriate purified by recrystallization.

The active compounds according to the invention have a strong microbicidal action and can be employed as fungicides in plant protection and in the protection of materials.

Fungicides are employed in plant protection for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as *Xanthomonas oryzae;*
Pseudomonas species, such as *Pseudomonas lachrymans;*
Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubense;*
Plasmopara species, such as *Plasmopara viticola;*
Peronospora species, such as *Peronospora pisi* or *P. brassicae;*
Erysiphe species, such as *Erysiphe graminis;*
Sphaerotheca species, such as *Sphaerotheca fuliginea;*
Podosphaera species, such as *Podosphaera leucotricha;*
Venturia species, such as *Venturia inaequalis;*
Pyrenophora species, such as *Pyrenophora teres* or *P. graminea* (conidia form: Drechslera,. syn: Helminthosporium);

Cochliobolus species, such as *Cochliobolus sativus* (conidia form: Drechslera, syn: Helminthosporium);
Uromyces species, such as *Uromyces appendiculatus;*
Puccinia species, such as *Puccinia recondita;*
Tilletio species, such as *Tilletia caries;*
Ustilago species, such as *Ustilago nuda* or *Ustilago avenae;*
Pellicularia species, such as *Pellicularia sasakii;*
Pyricularia species, such as *Pyricularia oryzae;*
Fusarium species, such as *Fusarium culmorum;*
Botrytis species, such as *Botrytis cinerea;*
Septoria species, such as *Septoria nodorum;*
Leptosphaeria species, such as *Leptosphaeria nodorum;*
Cercospora species, such as *Cercospora canescens;*
Alternaria species, such as *Alternaria brassicae* and
Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are suitable in plant protection, in particular, for combating cereal and rice diseases. Thus, powdery mildew and rust diseases, such as Erysiphe, *Leptosphaeria nodorum, Pyrenophora teres, Cochliobolus sativus* and *Fusarium nivale* on cereals and also Pyricularia and Pellicularia on rice can be particularly well combated. The substances can additionally be used against *Botrytis cinerea*, true mildew on cucumbers and also against Venturia on apples; they additionally have a very good in-vitro action.

In the protection of materials, the active compounds according to the invention can be employed for the protection of industrial materials. Industrial materials are in this connection taken to mean non-living materials which have been prepared for use in industry. For example, industrial materials which it is intended to protect from microbial change or destruction by use of the active compounds according to the invention can be adhesives, glues, paper, cardboard, textiles, leather, wood, paints, plastic articles, cooling lubricants and other materials which can be attacked or decomposed by microorganisms. In the context of the materials to be protected, parts of production plants, for example cooling water circulations, may also be mentioned, which may be impaired by replication of microorganisms. In the context of the present invention, technical materials which may be mentioned are preferably adhesives, glues, papers and cardboards, leather, wood, paints, cooling lubricants and cooling circulations, particularly preferably wood.

Microorganisms which may cause a degradation or a change in the industrial materials may be, for example, bacteria, fungi, yeasts, algae and slime organisms. The active compounds according to the invention preferably act against fungi, in particular Hyphomycetas, wood-discolouring and wood-destroying fungi (Basidiomycetes), and also against slime organisms and algae.

Microorganisms which may be mentioned are those of the following orders:
Alternaria, such as *Alternaria tenuis,*
Aspergillus, such as *Aspergillus niger,*
Chaetomium, such as *Chaetomium globosum,*
Coniophora, such as *Coniophora puteana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylocuccus, such as *Staphylococcus aureus.*

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, moleybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

When using the substances according to the invention as fungicides, the amounts applied can be varied within a relatively wide range depending on the type of application. Thus, in the treatment of parts of plants, the active compound concentrations in the use forms are, in general, between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02% by weight, are required at the place of action.

The preparation and the use of the active compounds according to the invention follows from the examples below.

PREPARATION EXAMPLES

Example 1

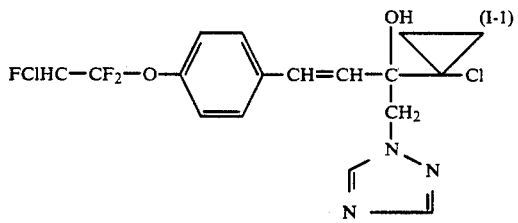

3.90 g (0.011 mole) of 2-(1-chloro-cyclopropyl)-2-[4-(2-chloro-1,1,2-trifluoroethoxy)-phenylethenyl]oxirane in 20 ml of dimethylformamide are added dropwise to a solution warmed to 80° C. of 2.96 g (0.043 mole) of 1,2,4-triazole and 0.48 g (0.0043 mole) of potassium tert.-butoxide in 30 ml of dimethylformamide. The reaction mixture is subsequently stirred for 12 hours at 80° C. and then concentrated by stripping off the solvent under reduced pressure. The residue is taken up in ethyl acetate, and the resulting solution is washed three times with water, dried over sodium sulphate and concentrated under reduced pressure. The residue which remains is chromatographed on a silica gel column using a mixture of cyclohexane: ethyl acetate =1:1. After evaporating the eluate, 3.2 g (69% of theory) of 2-(1-chlorocyclopropyl)-4-[4-(2-chloro-1,1,2 -trifluoroethoxy)-phenyl]-1-(1,2,4-triazol-1-yl)-but-3-en-2-ol are obtained in the form of a solid substance of melting point 113°–118° C.

Preparation of Starting Materials

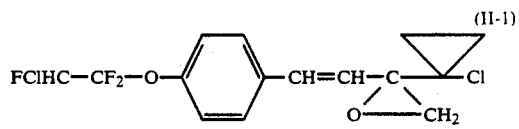

A solution of 6.35 g (0.031 mole) of trimethylsulphoxonium iodide in 20 ml of dimethyl sulphoxide is added at −15° C. with stirring to a suspension of 0.75 g (0.031 mole) of sodium hydride in 25 ml of a mixture of dimethyl sulphoxide: tetrahydrofuran =3:2. After warming the reaction mixture to 0° C., a solution of 9.6 g (0.028 mole) of 1-chloro-cyclopropyl 4-(2-chloro-1,1,2-trifluoroethoxy)-phenyl-ethenyl ketone in 15 ml of dimethyl sulphoxide is added dropwise with stirring. The mixture is subsequently stirred at 0° C. for 15 minutes and at room temperature for 45 minutes. The reaction mixture is then poured into 100 ml of ice water and the mixture is extracted three times with cyclohexane. The combined organic phases are washed once with water, dried over sodium sulphate and then concentrated under reduced pressure. 8.89 g (89% of theory) of 2-(1-chloro-cyclopropyl)-2-[4-(2-chloro-1,1,2-trifluoroethoxy)-phenylethenyl]-oxirane are obtained in this way in the form of an oily product which is reacted further without additional purification.

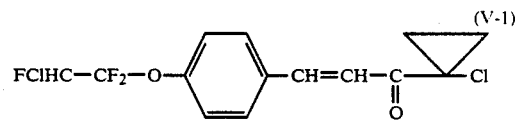

0.6 g (0.011 mole) of potassium hydroxide powder is added at room temperature to a solution of 24.3 g (0.102 mole) of 4-(2-chloro-1,1,2-trifluoroethoxy)-benzaldehyde and to 12.1 g (0.102 mole) of 1-chloro-cyclopropyl methyl ketone in 100 ml of tetrahydrofuran and the mixture is then stirred at 40° to 50° C. for 8 hours. The reaction mixture is then poured into a saturated aqueous ammonium chloride solution and the mixture is extracted twice with cyclohexane. The combined organic phases are dried over sodium sulphate and concentrated under reduced pressure. The residue which remains is chromatographed on silica gel using a mixture of cyclohexane:ethyl acetate =10:1 as eluent. By evaporating the eluate, 17 g (49% of theory) of 1-chloro-cyclopropyl 4-(2-chloro-1,1,2-trifluoroethoxy)-phenyl-ethenyl ketone are obtained in the form of an oily product.

IR spectrum (CHCl$_3$): Bands at 1580, 1600 and 1670 cm$^{-1}$

Example 2

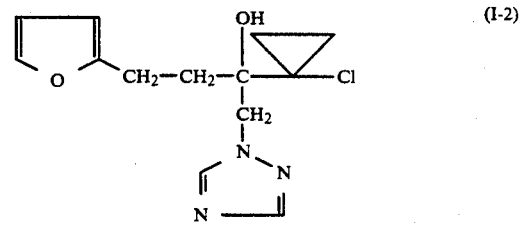

10.71 g (0.054 mole) of 2-(1-chloro-cyclopropyl)-2-(furan-2-yl-ethyl)-oxirane are added dropwise with stirring to a solution heated to 80° C. of 10.43 g (0.151 mole) of 1,2,4-triazole and 1.12 g (0.01 mole) of potassium tert.-butoxide in 80 ml of dimethylformamide. The reaction mixture is subsequently stirred at 80° C. for 6 hours and then concentrated by stripping off the solvent under reduced pressure. The residue which remains is taken up in ethyl acetate, and the organic phase is washed twice with water, dried over sodium sulphate and concentrated under reduced pressure. The residue which remains is chromatographed on silica gel using a mixture of cyclohexane: ethyl acetate 1:1 as eluent. After concentrating the eluate, 7.87 g (55% of theory) of 2-(1-chloro-cyclopropyl)-4-furan-2-yl-ethyl)-1-(1,2,4-triazol-1-yl)-butan-2-ol are obtained in the form of a solid substance of melting point 83°–86° C.

Preparation of Starting Materials

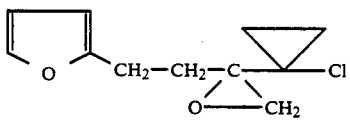
(II-2)

A solution of 11.3 g (0.055 mole) of trimethylsulphonium iodide in 50 ml of dimethyl sulphoxide is added dropwise with stirring to a suspension cooled to −15° C. of 1.33 g (0.055 mole) of sodium hydride in 75 ml of a mixture of dimethyl sulphoxide: tetrahydrofuran =1:2. After warming the reaction mixture to 0° C., a solution of 10.0 g (0.05 mole) of 1-(chloro-cyclopropyl)-furan-2-yl-ethyl ketone in 20 ml of dimethyl sulphoxide is added dropwise with stirring. The mixture is subsequently stirred at 0° C. for 10 minutes and at room temperature for 1 hour. The reaction mixture is then poured into iced water and the mixture is extracted three times with cyclohexane. The combined organic phases are dried over sodium sulphate and concentrated under reduced pressure. 10.27 g (96% of theory) of 2-(1-chloro-cyclopropyl)-2-(furan-2-yl-ethyl)-oxirane are obtained in this way in the form of an oily product which is reacted further without additional purification.

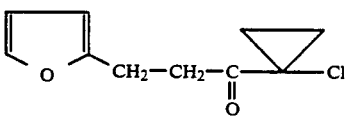
(V-2)

740 mg of tris-triphenylphosphine-rhodium chloride are added to a 0.3 l autoclave. After flushing the autoclave with nitrogen, an air-free solution of 17 g of 1-chloro-cyclopropyl 4-(furan-2-yl-)-ethenyl ketone in 150 ml of toluene is added and the mixture is heated to 50° C. under a hydrogen pressure of 30 bar. The hydrogen pressure is kept between 50 and 60 bar until the gas uptake is complete. The mixture is then allowed to react further for 1 hour. For working up, the solvent is stripped off under reduced pressure. The residue which remains is chromatographed on silica gel using dichloromethane as eluent. After evaporating the eluate, 14.7 g (86% of theory) of 1-chloro-cyclopropyl 4-(furan-2-yl)-ethyl ketone are obtained in the form of an oily product.

$^1$H-NMR spectrum (200 MHz, CDCl$_3$):

δ=1.35 (m, 2H); 1.65 (m, 2H); 2.9 (t, 2H); 3.2 (t, 2H); 6.0 (m,1H); 6.3 (m, 1H); 7.3 (m, 1H).

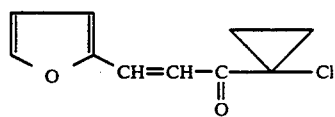
(V-3)

0.95 g (0.017 mole) of potassium hydroxide powder is added at room temperature to a solution of 20.0 g (0.169 mole) of 1-chloro-cyclopropyl methyl ketone and 14.0 ml (0.169 mole) of furan-2-carbaldehyde in 100 ml of tetrahydrofuran and the mixture is stirred at room temperature for 18 hours. The reaction mixture is poured into saturated aqueous ammonium chloride solution and the mixture is extracted three times with cyclohexane. The combined organic phases are dried over sodium sulphate and concentrated under reduced pressure. 34.0 g (100% of theory) of 1-chloro-cyclopropyl 4-(furan-2-yl)-ethenyl ketone are obtained in this way in the form of an oil.

IR spectrum (film):

Bands at 1550, 1600 and 1680 cm$^{-1}$

Example 3

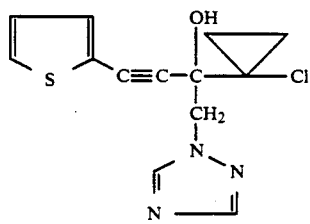
(I-3)

47.0 g (0.18 mole) of 1-chloro-2-(1-chlorocyclopropyl)-4-(thiophen-2-yl)-but-3-in-2-ol is added to a suspension of 100 g (0.72 mole) of potassium carbonate and 24.8 g (0.36 mole) of 1,2,4-triazole in 300 ml of acetone and the mixture is heated under reflux for 2 hours. The solvent is then stripped off under reduced pressure, and the residue which remains is taken up in water and extracted three times with dichloromethane. The combined organic phases are dried over sodium sulphate and concentrated under reduced pressure. The residue which remains is chromatographed on silica gel using a mixture of cyclohexane/ethyl acetate =1:1 as eluent. After evaporating the eluate, 7.9 g (15% of theory) of 2-(1-chlorocyclopropyl)-4-(thiophen-2-yl)-1-(1,2,4-triazol-1-yl)-3-butin-2-ol are obtained in the form of an oily product.

$^1$H-MR spectrum (200 MHz, CDCl$_3$):

δ=1.00–130 (m, 4H]; 4.78 (AB-System), 2H); 6.98 (m, 1H); 7.18 (m, 1H); 7.30 (m, 1H); 7.96 (s, 1H); 8.36 (s, 1H).

Preparation of Starting Materials

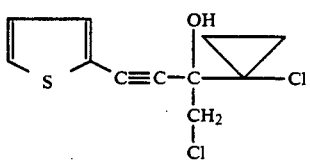
(IV-1)

22.2 g (0.203 mole) of ethyl bromide are slowly added to 4.9 g (0.203 mole) of magnesium turnings in 100 ml of diethyl ether. After completion of the addition, the reaction mixture is heated under reflux for 30 minutes and then cooled to room temperature, and a solution of 20 g (0.185 mole) of 2-thienylethine in 50 ml of diethyl ether is subsequently added dropwise with stirring. The mixture is heated under reflux for 1 hour and again cooled to room temperature. 28.3 g (0.185 mole) of 1-chloro-cyclopropyl chloromethyl ketone are added dropwise with stirring and the mixture is then heated under reflux for a further 2 hours. After cooling to room temperature, the reaction mixture is poured into a saturated aqueous ammonium chloride solution and the mixture is extracted three times with diethyl ether. The combined organic phases are washed once with water, dried over sodium sulphate and concentrated under reduced pressure. 47.0 g (97% of theory) of 1-chloro-2-(1-chlorocyclopropyl)-4-(thiophen-2-yl)-but-3-in-2-ol are obtained in this way in the form of an oil which is reacted further without additional purification.

Example 4

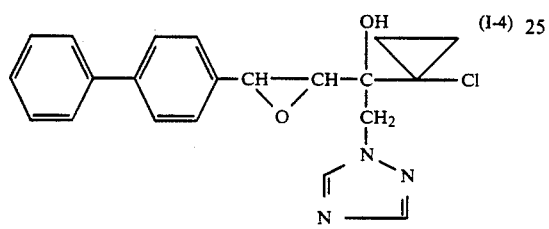
(I-4)

2.26 g (0.013 mole) of 3-chloro-perbenzoic acid are added at 0° C. to a solution of 4.0 g (0.011 mole) of 4-biphenyl-2-(1-chloro-cyclopropyl)-1-(1,2,4-triazol-1-yl)-but- 3-en-2-ol in 50 ml of dichloromethane and the mixture is stirred at room temperature for 5 hours. The reaction mixture is then washed three times with semisaturated aqueous sodium carbonate solution, dried over sodium sulphate and then concentrated under reduced pressure. The residue which remains is chromatographed on silica gel using a mixture of cyclohexane/ethyl acetate =1:1 as eluent. 2.7 g (64% of theory) of 4-biphenyl-2-(1-chloro-cyclopropyl)-3,4-epoxy-1-(1,2,4-triazol-1-yl)butan-2-ol are obtained in this way in the form of a solid having a melting point of 250°-254° C.

The compounds of the formula

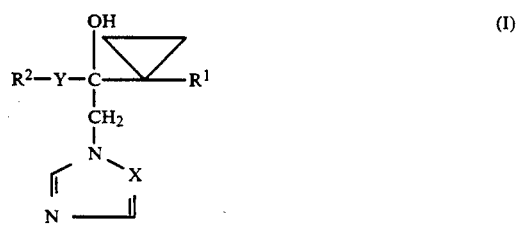
(I)

shown in the following Table 1 are also prepared according to the methods indicated in the preceding examples.

TABLE 1

| Example No. | Comp. No | R² | Y | X | R¹ | Physical or spectroscopic const. |
|---|---|---|---|---|---|---|
| 5 | I-5 | CH₂=CH—CH₂—C(CH₃)(CH₃)— | —CH=CH— | N | Cl | IR: 1700, 1730, 3000-3400 cm⁻¹ |
| 6 | I-6 | (furan-2-yl) | —CH=CH— | N | Cl | IR: 1730, 3100-3500 cm⁻¹ |
| 7 | I-7 | F₂HC—CF₂—O—(phenyl)— | —CH=CH— | N | Cl | IR: 1730, 3200-3400 cm⁻¹ |
| 8 | I-8 | F₂CH—O—(naphthyl) | —CH=CH— | N | Cl | IR: 1600, 1630, 3200-3400 cm⁻¹ |
| 9 | I-9 | (3-chlorophenyl)—CH₂—O—(phenyl)— | —CH=CH— | N | Cl | IR: 1600, 1720, 3200-3400 cm⁻¹ |

TABLE 1-continued

| Example No. | Comp. No | R² | Y | X | R¹ | Physical or spectroscopic const. |
|---|---|---|---|---|---|---|
| 10 | I-10 | 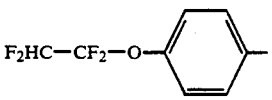 F₂HC—CF₂—O—⟨phenyl⟩— | —CH₂—CH₂— | N | Cl | IR: 1730, 3200–3400 cm⁻¹ |
| 11 | I-11 | 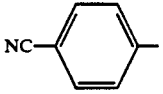 NC—⟨phenyl⟩— | —CH=CH— | N | Cl | m.p. 51–53° C. |
| 12 | I-12 | 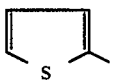 ⟨thiophene⟩— | —CH=CH— | N | Cl | IR: 1730, 3200–3400 cm⁻¹ |
| 13 | I-13 | 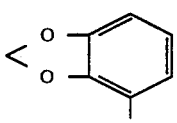 methylenedioxyphenyl— | —CH=CH— | N | Cl | IR: 1670, 1720, 3200–3400 cm⁻¹ |
| 14 | I-14 | 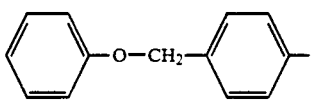 C₆H₅—O—CH₂—⟨phenyl⟩— | —CH=CH— cis | N | Cl | IR: 1600, 1660, 3200–3400 cm⁻¹ |
| 15 | I-15 | 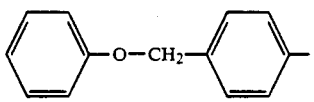 C₆H₅—O—CH₂—⟨phenyl⟩— | —CH=CH— trans | N | Cl | IR: 1600, 1720, 3200–3400 cm⁻¹ |
| 16 | I-16 | 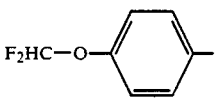 F₂HC—O—⟨phenyl⟩— | —CH=CH— | N | Cl | m.p. 48–49° C. |
| 17 | I-17 | 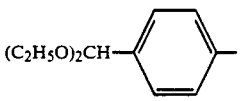 (C₂H₅O)₂CH—⟨phenyl⟩— | —CH=CH— | N | Cl | IR: 1720 cm⁻¹ 3200–3400 cm⁻¹ |
| 18 | I-18 | 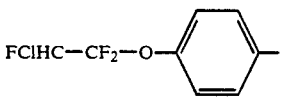 FClHC—CF₂—O—⟨phenyl⟩— | —CH=CH— | N | 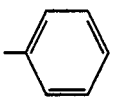 ⟨phenyl⟩ | IR: 1680, 1720, 3200–3400 cm⁻¹ |
| 19 | I-19 | 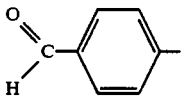 OHC—⟨phenyl⟩— | —CH=CH— | N | Cl | m.p. 87–88° C. |
| 20 | I-20 | 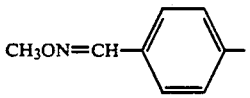 CH₃ON=CH—⟨phenyl⟩— | —CH=CH— | N | Cl | IR: 1700, 3200–3400 cm⁻¹ |
| 21 | I-21 | 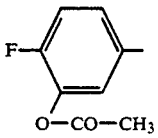 F, O—CO—CH₃ substituted phenyl— | —CH=CH— | N | Cl | m.p. 143–145° C. |
| 22 | I-22 | 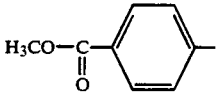 H₃CO—C(=O)—⟨phenyl⟩— | —CH=CH— | N | Cl | m.p. 128° C. |

TABLE 1-continued
| Example No. | Comp. No | R² | Y | X | R¹ | Physical or spectroscopic const. |
|---|---|---|---|---|---|---|
| 23 | I-23 |  | —CH₂—CH₂— | N | Cl | IR: 1730, 3200–3400 cm⁻¹ |
| 24 | I-24 | 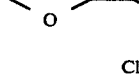 | —CH—CH— (epoxide) | N | Cl | IR: 1600, 1720 3200–3500 cm⁻¹ |
In the following are examples, the compounds of the formulae indicated below were employed as Comparison Examples:
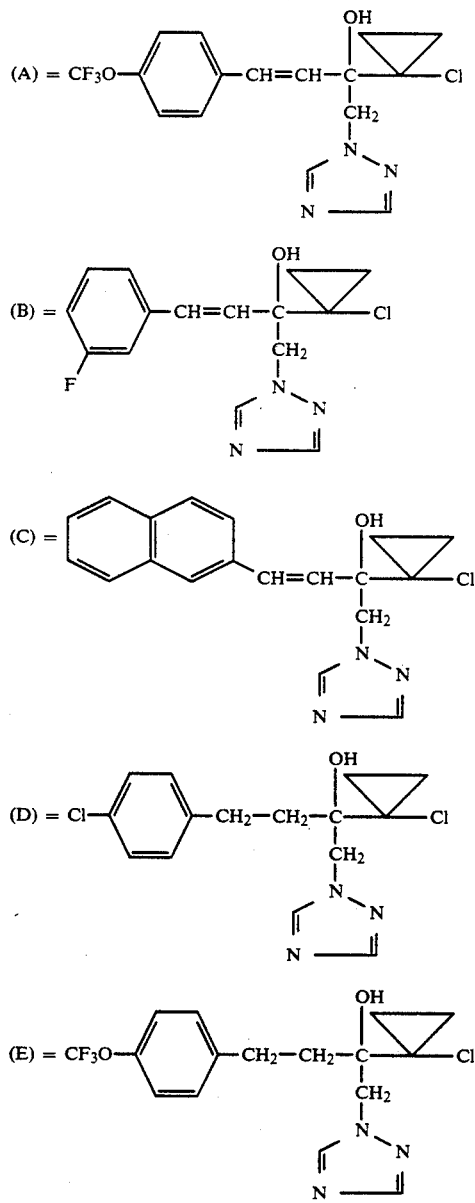
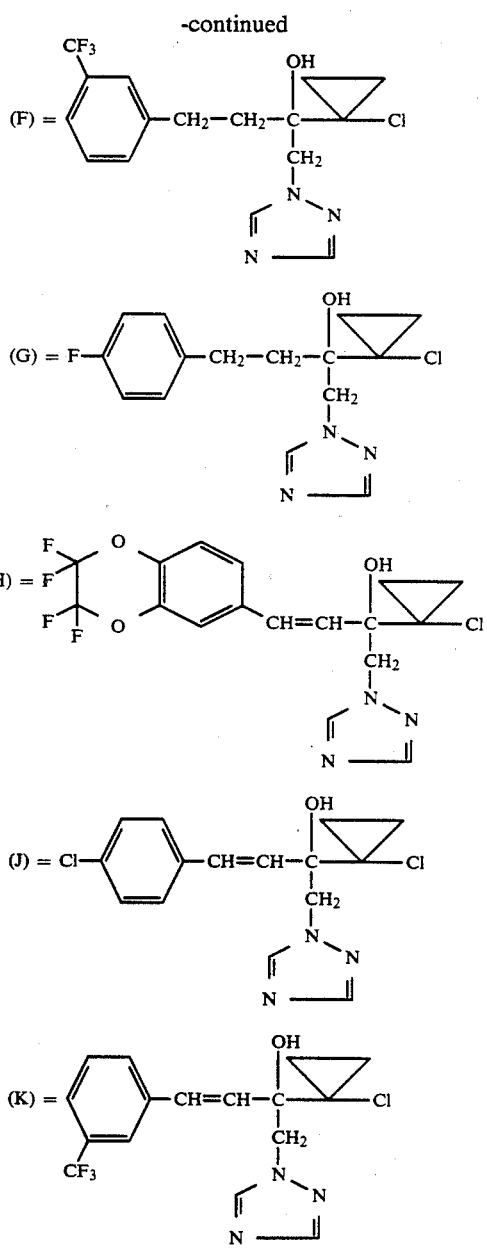
The comparison substances are known from EP-OS (European Published Specification) 0,298,332.

Example A

Erysiphe Test (Barley)/Protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compound (I-7) according to the invention shows a substantially better activity than the comparison substances (A), (B) and (C).

Example B

Cochliobolus Sativus Test (Barley)/Protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, the compound (I-10) according to the invention shows a substantially better activity than the comparison substances (D), (E) and (F).

Example C

Leptosphaeria Nodorum Test (Wheat)/Protective/

Solvent: 100 parts by weight of dimethylformamide
Emulsifier: 0.25 parts by weight of alkylaryl polyglycol ether To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of *Leptosphaeria nodorum*. The plants remain for 48 hours in an incubation cabin at 20° C. and at 100% relative atmospheric humidity.

The plants are placed in a greenhouse at a temperature of about 15° C. and a relative atmospheric humidity of about 80%.

Evaluation is effected 10 days after the inoculation.

In this test, for example, the substance (I-10) according to the invention shows a substantially better activity than the comparison substances (D), (F) and (G).

Moreover, in this test the compounds (I-1), (I-7), (I-8), (I-14), (I-19), (I-20) and (I-22) show a substantially better activity than the comparison substance (H).

Example D

Leptosphaeria Nodorum Test (Wheat)/Curative

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are sprayed with a spore suspension of *Leptosphaeria nodorum*. The plants remain for 48 hours in an incubation cabin at 20° C. and 100% relative atmospheric humidity. The plants are then sprayed with the active compound concentration until dew-moist.

The plants are placed in a greenhouse at a temperature of about 15° C. and a relative atmospheric humidity of about 80%.

Evaluation is effected 10 days after the inoculation.

In this test, the compound (I-7) according to the invention shows a substantially better activity than the comparison substance (J).

Example E

Pyrenophora Teres Test (Barley)/Protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Pyrenophora teres. The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, the compounds (I-1) and (I-13) according to the invention show a substantially better activity than the comparison substances (B) and (K).

Example F

Fusarium Nivale Test (Rye)/Seed Treatment

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 Batches of 100 grains of the rye are sown 1 cm deep in standard soil and are cultivated in a greenhouse at a temperature of about 10° C. and a relative atmospheric humidity of about 95%, in seed boxes which are exposed to light for 15 hours daily.

About 3 weeks after sowing, the plants are evaluated for symptoms of snow mold.

In this test, the compounds (I-1) and (I-7) according to the invention show a substantially better activity than the comparison substance (K).

Example G

Venturia Test (Apple) / Curative

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous conidia suspension of the apple scab causative organism (Venturia inaequalis). The plants remain in an incubation cabin at 20° C. and 100% relative atmospheric humidity for 1 day and are then placed in a greenhouse. After a given number of hours, the plants are sprayed with the preparation of active compound until dripping wet.

The plants are then placed in a greenhouse at 20° C. and a relative atmospheric humidity of about 70%.

Evaluation is carried out 12 days after the inoculation.

In this test, the compound (I-10) according to the invention shows a substantially better action than the comparison substances (F) and (G).

Moreover, in this test the compounds (I-1), (I-7) and (I-8) show a substantially better action than the comparison substances (B) and (K).

It will be appreciated that the instant specification and claims are set forth by way of illustration and not limitation, and that various modifications and changes may be made without departing from the spirit and scope of the present invention.

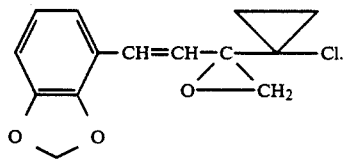

6. A compound according to claim 1, wherein such compound is 2-(1-chlorocyclopropyl)-2-[4-(1,1,2,2-tetrafluoroethoxy)-phenyl]-ethyl-oxirane of the formula
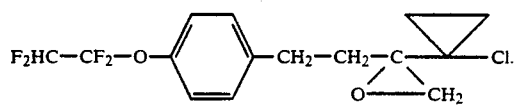

What is claimed is:

1. An oxirane of the formula

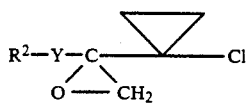

in which
R² represents furyl which is optionally substituted by furyl, or represents the radical of the formula

wherein
R⁴ represents difluoromethoxy, 1,1,2,2-tetrafluoroethoxy, 1,1,2-trifluoro-2-chloro-ethoxy, formyl, methoximinomethyl, methoxycarbonyl or phenoxymethyl and
R⁵ represents hydrogen, or
R⁴ and R⁵ are linked in the ortho-position and together represent —O—CH₂—O—, or
R² represents the radical of the formula

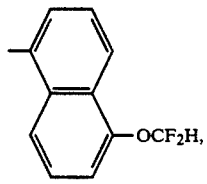

and
Y represents the grouping —CH₂—CH₂—, —CH=CH— or —C≡C—.

2. A compound according to claim 1, wherein such compound is 2-(1-chlorocyclopropyl)-2-[4-(2-chloro-1,1,2-trifluoroethoxy)-phenyl]-vinyl-oxirane of the formula

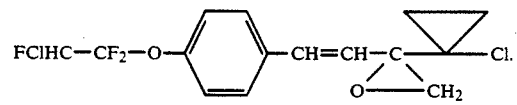

3. A compound according to claim 1, wherein such compound is 2-(1-chlorocyclopropyl)-2-[4-(1,1,2,2-tetrafluoroethoxy)-phenyl]-vinyl-oxirane of the formula

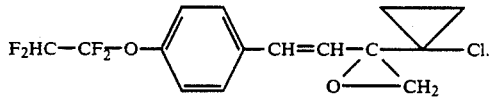

4. A compound according to claim 1, wherein such compound is 2-(1-chlorocyclopropyl)-2-[(5-difluoromethoxy)-naphth-1-yl]-vinyl-oxirane of the formula

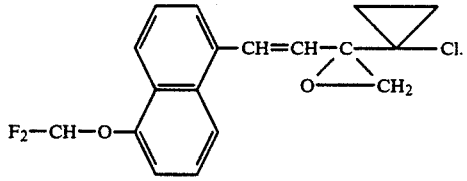

5. A compound according to claim 1, wherein such compound is 2-(1-chlorocyclopropyl)-2-(2,3-methylenedioxyphenyl-vinyl-oxirane of the formula